(12) United States Patent
Holmin et al.

(10) Patent No.: US 12,702,390 B2
(45) Date of Patent: Aug. 11, 2026

(54) BIOPSY DEVICE

(71) Applicant: MICROCARDIX AB, Sundbyberg (SE)

(72) Inventors: Staffan Holmin, Bromma (SE); Stefan Jonsson, Sollentuna (SE); Rikard Grankvist, Sundbyberg (SE); Mikael Sandell, Årsta (SE); Arvin Chireh, Stockholm (SE)

(73) Assignee: MICROCARDIX AB, Sundbyberg (SE)

(*) Notice: Subject to any disclaimer, the term of this patent is extended or adjusted under 35 U.S.C. 154(b) by 713 days.

(21) Appl. No.: 17/289,875

(22) PCT Filed: Oct. 31, 2019

(86) PCT No.: PCT/EP2019/079896
§ 371 (c)(1),
(2) Date: Apr. 29, 2021

(87) PCT Pub. No.: WO2020/089422
PCT Pub. Date: May 7, 2020

(65) Prior Publication Data

US 2021/0401413 A1 Dec. 30, 2021

(30) Foreign Application Priority Data

Nov. 2, 2018 (GB) ..................................... 1817970

(51) Int. Cl.
*A61B 10/02* (2006.01)

(52) U.S. Cl.
CPC ................................ *A61B 10/0266* (2013.01)

(58) Field of Classification Search
CPC ............ A61B 10/0266; A61B 10/0275; A61B 2010/045; A61B 10/0233
See application file for complete search history.

(56) References Cited

U.S. PATENT DOCUMENTS 3,001,522 A 9/1961 Silverman
5,171,255 A 12/1992 Rydell
(Continued)

FOREIGN PATENT DOCUMENTS

CN 102307529 A 1/2012
CN 105310729 A 2/2016
(Continued)

OTHER PUBLICATIONS

International Search Report and Written Opinion were mailed on Mar. 24, 2020 by the International Searching Authority for International Application No. PCT/EP2019/079896, filed on Oct. 31, 2019 and published as WO 2020/089422 on May 7, 2020 (Applicant—Microcardix AB) (15 Pages).

*Primary Examiner* — Jason M Sims
*Assistant Examiner* — Ari S Padda
(74) *Attorney, Agent, or Firm* — Ballard Spahr LLP

(57) ABSTRACT

Disclosed is a biopsy device having a tip member with a rearward facing cutting portion for use in a biopsy procedure. The biopsy procedure involves introducing and manoeuvring the device into the tissue of a subject and obtaining a biopsy sample. The biopsy device has an elongate flexible rod member having a proximal end and a distal end that define a first longitudinal axis, and a tip member having a proximal end and a distal end that define a second longitudinal axis. The tip member is located at or towards the distal end of the elongate member and positioned or positionable so that the longitudinal axis of the tip member is angularly offset with respect to the longitudinal axis of the elongate member. The distal end of the tip member is configured to penetrate tissue and the proximal end of the tip member has a cutting portion for cutting tissue.

23 Claims, 11 Drawing Sheets

(56) References Cited

U.S. PATENT DOCUMENTS

| | | | | |
|---|---|---|---|---|
| 5,385,570 | A | 1/1995 | Chin et al. | |
| 5,526,821 | A | 6/1996 | Jamshidi | |
| 5,827,305 | A | 10/1998 | Gordon | |
| 8,894,653 | B2 * | 11/2014 | Solsberg | A61B 10/0275 606/205 |
| 9,072,506 | B1 | 7/2015 | Seiger et al. | |
| 10,159,470 | B2 | 12/2018 | McWeeney et al. | |
| 2004/0138676 | A1 * | 7/2004 | Crabtree | A61B 17/3403 606/108 |
| 2009/0204021 | A1 | 8/2009 | Shabaz et al. | |
| 2010/0185116 | A1 * | 7/2010 | Al-Mohizea | A61B 10/0233 600/564 |
| 2010/0312141 | A1 * | 12/2010 | Keast | A61B 8/12 600/567 |
| 2011/0288437 | A1 * | 11/2011 | Ryan | A61B 10/0275 600/567 |
| 2013/0123662 | A1 * | 5/2013 | Hipp | A61B 10/025 600/564 |
| 2014/0163418 | A1 * | 6/2014 | Gigi | A61B 10/0266 600/567 |
| 2015/0011909 | A1 | 1/2015 | Holmin et al. | |
| 2015/0088032 | A1 * | 3/2015 | Lee-Sepsick | A61B 10/0291 600/570 |
| 2015/0223787 | A1 | 8/2015 | Coonahan et al. | |
| 2015/0265257 | A1 | 9/2015 | Costello et al. | |
| 2016/0030014 | A1 | 2/2016 | McWeeney | |
| 2016/0030016 | A1 * | 2/2016 | Mcweeney | A61B 10/0233 600/567 |
| 2016/0081673 | A1 * | 3/2016 | Wehbe | A61B 10/0266 600/567 |
| 2016/0199047 | A1 | 7/2016 | McWeeney et al. | |
| 2017/0245933 | A1 * | 8/2017 | Graham | A61B 17/29 |

FOREIGN PATENT DOCUMENTS

| | | |
|---|---|---|
| CN | 205339010 U | 6/2016 |
| WO | WO 2001/015609 | 3/2001 |

* cited by examiner

A

B

C

BIOPSY DEVICE

CROSS-REFERENCE TO RELATED APPLICATIONS

This application is a U.S. National Phase Application of International Application No. PCT/EP2019/079896, filed Oct. 31, 2019, which claims priority to Great Britain Application No. 1817970.5, filed Nov. 2, 2018, each of which are hereby incorporated by reference in their entirety.

The present invention is directed towards a biopsy device comprising a tip member with a rearward facing cutting portion for use in a biopsy procedure. The biopsy procedure involves introducing and manoeuvring the device into the tissue of a subject and obtaining a biopsy sample.

Endomyocardial biopsy is an established diagnostic modality used primarily in post-transplantation rejection monitoring, but also in a variety of cardiac pathologies such as cardiomyopathies, infectious diseases, and neoplastic disease. The biopsy rate for difficult diagnoses has been described as too low, in part owing to risks inherent in the procedure, and low diagnostic yield. Endomyocardial bioptomes are relatively large devices compared to other modern sub-millimetre sized endovascular interventional devices, which makes them traumatic and hard to steer to all parts of the heart as well as to other parts of the body if desired for biopsy purposes. In current practice, endomyocardial biopsies are, therefore, restricted to certain parts of the heart due to the inherent properties of those device.

As such, biopsy is generally limited to the septal wall of the right ventricle, whose myocardium may not be representative of the left ventricle (LV), where much of the hard-to-diagnose pathology resides. The present invention is directed towards a device which may be manufactured to be a smaller, more steerable bioptome that may allow easier and safer access to most parts of the LV myocardium, as well as other parts of the body, enabling biopsy with greater diagnostic yield and increased overall safety.

It is a further aim of the present invention to provide an improved biopsy device which is able to obtain smaller and more uniform tissue samples from any part of the heart whilst causing minimal damage to the tissue of the subject being sampled. The device may be used for any biopsy procedure and not just for obtaining a biopsy sample from the heart. For example, the device is also suitable for obtaining a biopsy sample from lung tumours by advancing the device through the endovascular system of a patient or the endobronchial system of a patient.

BRIEF DESCRIPTION OF THE INVENTION

According to the present invention, there is provided a biopsy device comprising:

- an elongate flexible rod member having a proximal end and a distal end that define a first longitudinal axis; and
- a tip member having a proximal end and a distal end that define a second longitudinal axis, the tip member being located at or towards the distal end of the elongate rod member and positioned or positionable so that the longitudinal axis of the tip member is angularly offset with respect to the longitudinal axis of the elongate rod member, wherein the distal end of the tip member is configured to penetrate tissue of a subject and the proximal end of the tip member comprises a cutting portion for cutting tissue of a subject.

According to another aspect of the invention, there is provided a kit-of-parts comprising a biopsy device as defined above in the form of a sterile, pre-packaged kit-of-parts for single use.

According to a further aspect of the invention, there is provided a method for obtaining a biopsy from a subject using a device as defined above wherein the method comprises:

- delivering the device as defined above to a body location;
- advancing the distal end of the tip member of the device into a tissue so that the entirety of the tip member advances into the tissue; and
- withdrawing the tip member from the tissue.

According to another aspect of the invention there is provided the use of a biopsy device as defined above for obtaining a biopsy from a subject.

According to a further aspect of the invention there is provided a method of manufacturing the device according to the invention.

According to another aspect of the invention, there is provided a method of sampling and/or analysing a tissue sample having a size of less than about 10 mg, preferably less than 0.1 mg, optionally wherein the sample has been obtained according to the method as described herein or by the use of the biopsy device as described herein.

Definitions

Proximal end: defines the end of the relevant portion of the biopsy device that is the closest to the medical practitioner when the device is in use.

Distal end: defines the end of the relevant portion of the biopsy device that is the farthest away to the medical practitioner when the device is in use.

Rod member longitudinal axis: axis along the length of the rod member that is defined by the distal and proximal ends of the rod member. The rod member may be flexible and, therefore, the longitudinal axis need not be straight, but may also extend along a curved pathway when the rod member is in a bent configuration.

Tip member longitudinal axis: axis along the length of the tip member that is defined by the distal and proximal ends of the tip member.

Angular offset between rod member and tip member: the tip member is positioned or positionable so that the longitudinal axis of the tip member is angularly offset with respect to the longitudinal axis of the elongate rod member, meaning that the longitudinal axis of the tip member and elongate rod member cross at a single point. The person skilled in the art would appreciate that the longitudinal axes do not have to actually cross. For example, in embodiments where the tip member and elongate rod member are connected by a hinge portion meaning that the tip member and elongate rod member are not physically attached to one another, their longitudinal axes do not physically cross. However, if the longitudinal axes were extended past the distal and proximal ends of the rod member and tip member, they would inevitably cross at a single point and would be angularly offset to one another.

BRIEF DESCRIPTION OF THE DRAWINGS

The embodiments of the invention, together with its advantages, may be best understood from the following detailed description taken in conjunction with the accompanying figures where same features are represented by the same numerals.

DETAILED DESCRIPTION OF THE INVENTION

Figure 1:
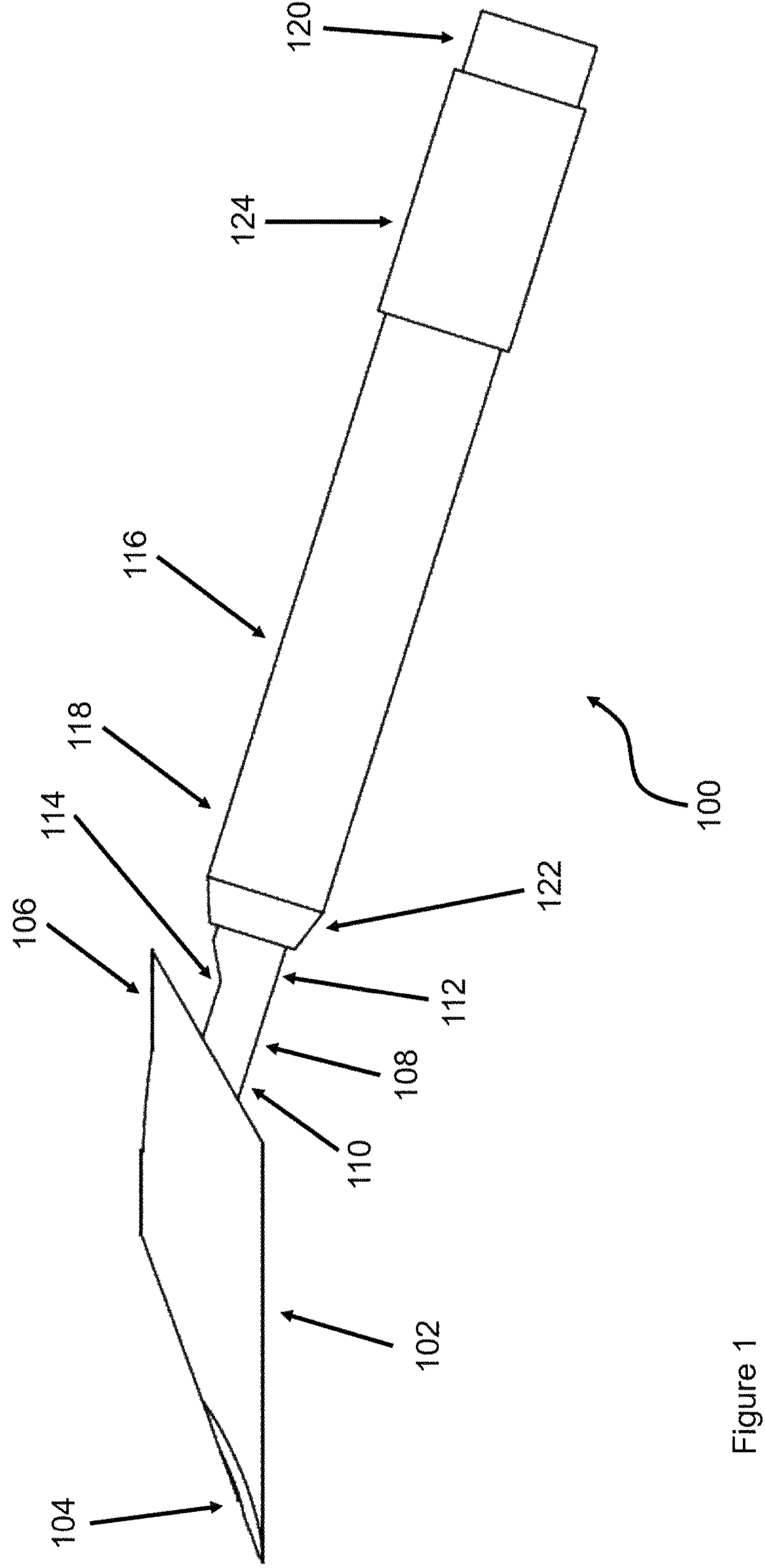
FIG. 1 is a side view of an embodiment of the inventive biopsy device.

The invention should not be construed as being limited to any of the following embodiments or any of the features described in these embodiments except to those features present in the independent claims. Furthermore, it is envisaged that all features in the embodiments may be combined with other features in other embodiments where appropriate and reasonably plausible.

According to the present invention, a biopsy device is disclosed comprising an elongate flexible rod member having a proximal end and a distal end that define a first longitudinal axis. The device also comprises a tip member having a proximal end and a distal end that define a second longitudinal axis.

The tip member is located at or towards the distal end of the elongate rod member and positioned, or positionable, so that the longitudinal axis of the tip member is angularly offset with respect to the longitudinal axis of the elongate member. By the term 'located towards' we mean that the tip member is located at the distal end of the rod member and is either connected directly to the rod member or is connected via a connecting portion, such as a hinge section.

The distal end of the tip member is configured so as to be able to penetrate tissue of a subject and the proximal end of the tip member comprises a cutting portion for cutting tissue of a subject. Preferably, the distal end of the tip member is in the form of a sharpened tip which is capable of penetrating the tissue of a subject. For example, the distal end of the tip member may be in the form of a conical tip, a bevel tip or a franseen (triangular) tip.

In an embodiment, the distal end of the tip member is solid, that is to say that it does not comprise a hollow lumen and/or that the face of the distal end of the tip member that is capable of penetrating the tissue of a subject is solid.

Conveniently, the distal end of the tip member is in the form of a bevelled tip at an acute angle with respect to the longitudinal axis of the tip member for penetrating the tissue of a subject. In such an embodiment, the acute angle may be from about 1° to about 45°, for example from about 1° to about 30°, such as from about 5° to about 30°, preferably from about 10° to about 30° and more preferably from about 10° to about 20°.

Preferably, the overall length of the tip member (i.e., the length from the very end of the distal portion of the tip member to the very end of the proximal portion of the tip member) is from about 500 μm to about 5000 μm, for example from about 1000 μm to about 4000 μm, such as from about 1000 μm to about 3000 μm.

Advantageously, the width of the tip member is from about 100 μm to about 1000 μm, such as from about 100 μm to about 500 μm, for example from about 200 μm to about 500 μm, preferably from about 300 μm to about 500 μm.

As for the rod member, the width of this member is preferably from about 50 μm to about 500 μm, such as from about 100 μm to about 400 μm, for example from about 100 μm to about 300 μm, preferably from about 200 μm to about 300 μm. There is no limitation on the length that the rod member may be.

In use, the device is delivered to a bodily site of a subject. For example, the device may be delivered to a bodily site of a subject through the use of a guide catheter. Guide catheters are hollow flexible tubes for insertion into a body cavity, duct or vessel. Guide catheters generally have a length of at least about 100 cm and in some cases up to about 150 cm. In use, the distal end of the guide catheter is advanced through the body cavity towards the bodily site of interest. On being delivered to the bodily site of interest, the biopsy device according to the invention can be introduced through an entry port located at the proximal end of the guide catheter and advanced through the lumen of the guide catheter.

Preferably, the device (and guide catheter if used) is advanced to the bodily site of interest through the patient's endovascular or endobronchial system.

On reaching the distal end of the guide catheter, the biopsy device can then be advanced out of an exit port of the guide catheter located at the distal end thereof. The distal end of the tip member is the first portion of the biopsy device that exits the exit port of the guide catheter so that on further advancement, the tip member penetrates the tissue of the bodily site of interest.

Optionally, the biopsy device may be housed within a micro-catheter, which is itself located within the guide catheter. When advancing the device out of the guide catheter, this may be done simultaneously with the micro-catheter and, once the device has exited the guide catheter, it may be further advanced whilst the micro-catheter is retained in position (or retracted) to expose the device.

On penetrating the tissue, the device is further advanced to a tissue depth from which it is desired that a sample be taken. When penetrating the tissue, in one embodiment, the longitudinal axis of the tip member and the longitudinal axis of the rod member may overlap. That is to say, the tip member and rod member may be positioned so as to be extending in predominantly the same direction and along the same axis. On reaching the desired tissue depth, it is at this point that the tip member may be manipulated, through pulley wires for example, so as to offset the longitudinal axis of the tip member with respect to the longitudinal axis of the elongate member. For example, in this embodiment, the tip member may be connected to the rod member through a hinged section around which the tip member may pivot.

Alternatively, the tip member and rod member may be rigidly fixed to one another so that when the tip member penetrates the tissue of the subject, the longitudinal axis of the tip member is already angularly offset to the longitudinal axis of the rod member at the desired angle.

Therefore, the term 'positionable' is envisaged to encompass scenarios where the tip member and rod member are rigidly fixed to one another so that their longitudinal axes are permanently offset and where the tip member is located on the rod member and is able to be manipulated so as to change the offset angle between the two longitudinal axes.

Furthermore, the rod member and/or tip member may be rigid themselves, that is to say that the material that they are made out of is substantially rigid.

Preferably, the longitudinal axis of the tip member is positioned or positionable so as to be offset at an angle of from about 1° to about 60° with respect to the longitudinal axis of the elongate rod member. For example, the offset angle may be from about 1° to about 50°, such as from about 1° to about 40°, or from about 1° to about 20°. Preferably the offset angle may be from about 5° to about 20° and more preferably from about 10° to about 20°. Ideally the offset angle is 60° or below so as to allow the distal end of the tip member to easily penetrate tissue and to still enable the cutting portion to penetrate tissue not penetrated by the distal end of the tip member when the device is retracted from the tissue.

As detailed above, the distal end of the device comprises a cutting portion for cutting tissue of a subject. With the longitudinal axis of the tip member being angularly offset to the longitudinal axis of the rod member, this allows for the cutting portion of the tip member to cut tissue which has not been damaged by the distal end of the tip on penetration and also allows for a more uniform sample to be taken as the tissue sample will be taken away from the hole created by the penetration.

Advantageously, the cutting portion of the tip member comprises a pointed blade, wherein the point of the blade extends substantially in the proximal direction of the longitudinal axis of the tip member. That is to say, the point of the blade extends in a direction which is within 20°, such as within 15°, 10° or 5°, of the direction of the longitudinal axis of the tip member.

Conveniently, the cutting portion of the tip member comprises two pointed blades, wherein the points of the blades extend substantially in the proximal direction (with the term 'substantially' being described in the previous paragraph) of the longitudinal axis of the tip member.

Preferably, the blades extend parallel to one another in substantially the proximal direction of the longitudinal axis of the tip member.

Where the cutting portion is in the form of a pointed blade or multiple blades, the length of the blade(s) is preferably from about 100 μm to about 2000 μm, for example from about 100 μm to about 1000 μm, such as from about 100 μm to about 500 μm, preferably from about 200 μm to about 500 μm and more preferably from about 200 μm to about 400 μm.

The cutting portion may also be in the form of a bevelled edge at an acute angle with respect to the longitudinal axis of the tip member. Preferably, where both the penetrating portion and cutting portion are in the form of a bevel, the points of the bevel extend in diametrically opposed directions. That is to say, when viewed from a side angle the tip member takes the form of a parallelogram or pseudo-parallelogram (if the bevel angles are not identical).

In such an embodiment where the cutting portion is in the form of a bevelled edge, which may also comprise a pointed blade(s) as detailed herein, the acute angle may be from about 1° to about 45°, for example from about 1° to about 35°, such as from about 5° to about 35°, preferably from about 10° to about 35° and more preferably from about 20° to about 35°.

Advantageously, the cutting portion comprises two single-edged blades that are facing each other, wherein the blades are spaced apart from each other so as to define a void or a slit in the cutting portion between the blades. Preferably, the width of the void is from about 50 μm to about 500 μm, for example from about 50 μm to about 400 μm, such as from about 50 μm to about 300 μm, preferably from about 100 μm to about 300 μm.

One additional advantage of the invention is that due to the unique configuration of the device, a much more reliable and uniform sample size is obtained than currently used biopsy devices.

One additional advantage of the invention is that the design allows the device to be produced and functional in small dimensions so that the entire device fits into a micro-catheter, which makes the system flexible and minimally invasive.

Furthermore, the sample obtained by the present device is much less damaged than samples obtained by currently used devices. As a result, the device may be manufactured to be much smaller than currently used biopsy devices and, therefore, the sample of tissue obtained by the inventive device can have a mass in the milligram, or even sub-milligram, range whilst still being suitable for cytological and biochemical evaluation, including transcriptomic, proteomic and genetic analysis. For example, the sample mass obtained by the device according to the invention may be less than about 10 mg, such as less than about 9, 8, 7, 6, 5, 4, 3, 2, or 1 mg. Preferably, the sample mass obtained by the device is in the range of from about 0.01 mg to about 5 mg, such as from about 0.01 to about 1 mg, and about 0.01 to about 0.1 mg.

This has the additional benefit that the device of the invention may cause much less damage to the tissue, both the sample tissue and the tissue remaining in the body, than currently used devices.

Furthermore, due to the ability to manufacture the device to much smaller dimensions than currently used devices, the inventive device may be used to access and sample tissues which cannot be accessed by currently used devices.

After reaching the desired depth within the tissue of interest, the advancement of the biopsy device into the tissue is halted. If not already positioned so, the longitudinal axis of the tip member is then angularly offset to the longitudinal axis of the rod member. After which, a sample of the tissue is obtained by using the cutting portion of the tip member.

Preferably, to obtain the sample, the tip member is first rotated after advancement and then retracted in the proximal direction. There is no limitation on the amount of rotation that is required to obtain the sample and this is dependent on the specific circumstances. For example, the device may be rotated by 90°, 180°, 270° or even a full 360°. Equally, there is no limitation on which direction the device is rotated in, either clockwise or anticlockwise and this will depend on the configuration of the cutting portion.

Conveniently, the rod member comprises a trough located at its distal end and preferably, the trough of the rod member is positioned opposite to and facing the cutting portion of the tip member. Where the device comprises a void in the cutting portion, the trough may also be positioned to be opposite to and facing the void. The trough member advantageously provides further space to retain the tissue sample after the cutting portion has cut a sample of tissue.

Preferably, the depth of the trough is about 20% to 70% the width of the rod member, such as from about 20% to about 60% the width of the rod member, preferably from about 30% to about 50% the width of the rod member.

Advantageously, the rod member is slidably and rotatably disposed within the lumen of a sheath member, wherein the sheath comprises a proximal end and a distal end, with the rod member extending from the distal end of the sheath member.

In an embodiment, the sheath member has an outer diameter of from about 100 μm to about 1000 μm, such as from about 100 μm to about 500 μm, for example from about 200 μm to about 500 μm, preferably from about 300 μm to about 500 μm.

Preferably, the lumen of the sheath member has a diameter of from about 100 μm to about 1000 μm, such as from about 100 μm to about 500 μm, for example from about 200 μm to about 500 μm, preferably from about 200 μm to about 400 μm. In any case, the diameter of the lumen of the sheath member is smaller than the outer diameter of the sheath member.

Conveniently, the sheath member comprises an anvil at the distal end of the sheath member such that it can form a blade and anvil relationship with the cutting portion of the tip member in use. Preferably, the anvil extends around at least part of, or preferentially the entire edge of, the lumen at the distal end of the sheath member. More preferably, the anvil is uniform and symmetric around the entire edge of the lumen at the distal end of the sheath member. By the term 'anvil' we mean that the distal end of the sheath member is a blunt edge, or is a sharpened edge, for example a bevelled edge.

Preferably, the anvil is in the form of a bevelled edge (which may be sharpened) that forms an acute angle of from about 1° to about 45°, for example from about 1° to about 30°, such as from about 5° to about 30°, preferably from about 10° to about 30° and more preferably from about 10° to about 20°.

In embodiments where the biopsy device comprises a sheath member, the rod member may be in a retracted position prior to penetration of the tissue so that the proximal end of the tip member abuts the distal end of the sheath member. That is to say, the rod member is retracted within the sheath member so that the proximal end of the tip member comes to a stop when it reaches, and rests against, the distal end of the sheath member. However, the distal end of the tip member remains outside of the sheath member so that the tip may penetrate tissue on advancement. The device may be retained in this configuration while it is advanced into the tissue and the tip member, rod member and sheath are advanced together, with the proximal end of the tip member penetrating the tissue of interest first. On reaching a certain predefined depth, the passage of the sheath member into the tissue may be halted and the tip member and rod member of the device may be further advanced into the tissue and out of the sheath.

On reaching the ultimate desired tissue depth, the tissue sample may be obtained as detailed above by rotating the tip member. After rotation, the rod member may be retracted within the sheath member and the cutting portion of the proximal part of tip member thereby cuts a section of tissue and, as the rod member is retracted within the sheath, the anvil of the sheath member may act as a further cutting edge to cut the tissue and retain, within the trough of the rod, a sample of the desired size.

In an alternative embodiment, the rotation of the tip member to cut the tissue and the retraction of the rod member into the sheath may be carried out simultaneously. In either embodiment, after the rod has been retracted within the sheath so that the proximal end of the tip member abuts the distal end of the sheath as outlined above, the device is then retracted out of the tissue and ultimately retracted out of the body of the subject.

An advantage of retracting the rod member back into the sheath, and the tip member towards the distal part of the sheath member, is that the sample of tissue is housed within the sheath, at least partially, preferably within the trough of the rod member, so that on retraction the sample is secure and is not able to escape. For example, if the device is being used to obtain a sample of heart tissue, then if the sample was not secured it could potentially escape into the endovasculature of the patient and cause an embolism.

Advantageously, the sheath member comprises a collar which acts as an intrusion depth limitation member located proximally of the distal end. For example, the collar may be in the form of a projecting rim to provide the user with a defined stopping point to aid the correct insertion of the sheath to the desired depth in the tissue.

Preferably, the collar may have a total width of from about 100 μm to about 2000 μm, such as from about 100 μm to about 1000 μm, for example from about 500 μm to about 1000 μm, preferably from about 500 μm to about 800 μm.

The collar may be rigidly fixed to the sheath member or, alternatively, the collar may be moveable on the sheath member so as to allow the user to tailor the depth to which the sheath will penetrate the tissue in use. For example, the collar may be slidable around the outer circumference of the sheath. As another example, the outside of the sheath may comprise a screw thread extending around its circumference and the collar may be a tube with an internal lumen that also comprises a screw thread opposite to the thread of the sheath and configured so that the collar may be threaded onto the sheath. This would allow for the user to tailor the depth that the sheath member penetrates to in use and provides a more versatile device.

Conveniently, the collar is comprised of a metal, preferably gold, platinum or other radiopaque metal.

Preferably, any of the components of the device, including the tip member, rod member and/or sheath member may, independently, be composed of a shape memory alloy, preferably Nitinol which is an alloy of nickel and titanium. Advantageously, the memory shape alloy is composed of from about 20 wt. % to about 60 wt % titanium and from about 80 wt. % to about 40 wt. % nickel, such as from about 30 wt. % to about 50 wt % titanium and from about 70 wt. % to about 50 wt. % nickel, preferably from about 40 wt. % to about 50 wt % titanium and from about 60 wt. % to about 50 wt. % nickel.

According to another aspect of the invention, there is provided a kit-of-parts comprising a biopsy device as defined above in the form of a sterile, pre-packaged kit-of-parts for single use. Preferably, the kit further comprises a micro-catheter and/or a guide catheter and these further components, along with any other components in the kit, may be provided in the same pack as the biopsy device or in a separate pack.

It is also envisaged that the device itself may be supplied in separate parts in the kit (i.e., rod member, tip member and sheath member) and the user assembles the device prior to use.

According to a further aspect of the invention, there is provided a method for obtaining a biopsy from a subject using a device as defined above wherein the method comprises:

delivering the device as defined above to a body location;
advancing the distal end of the tip member of the device into a tissue so that the entirety of the tip member advances into the tissue; and
withdrawing the tip member from the tissue.

The method of use may comprise any of the steps detailed above.

Preferably, after penetrating the tissue and prior to retraction, the tip member is rotated in the tissue.

Advantageously, where the device comprises a sheath portion on advancing the device into the tissue, the rod member is retracted within the sheath portion so that the proximal end of the tip member abuts the distal end of the sheath portion.

Conveniently, after advancing the device into the tissue, the rod member is extended out of the sheath portion thereby making the tip and rod members penetrate further into the tissue.

Preferably, upon withdrawing the tip member from the tissue, the rod member is first retracted into the sheath portion and optionally, when the biopsy device comprises a sheath member with an anvil located at the distal end, this may provide a blade and anvil relationship with the cutting portion of the tip member in use.

Advantageously, the sample mass obtained by the device when being used according to the invention may be less than about 10 mg, such as less than about 9, 8, 7, 6, 5, 4, 3, 2, or 1 mg. Preferably, the sample mass obtained by the device is in the range of from about 0.01 mg to about 5 mg, such as from about 0.01 to about 1 mg, and about 0.01 to about 0.1 mg.

According to another aspect of the invention there is provided the use of a biopsy device according as defined above for obtaining a biopsy from a subject.

According to a further aspect of the invention there is provided a method of manufacturing the device according to the invention.

As described above, the device according to the invention may be used for obtaining tissue samples from many parts of a patient, such as the heart or lung, and the size of the device may be modified depending on its intended use.

An advantage of the present device is that it can be manufactured to sizes that are much smaller than currently used bioptomes and, therefore, the sample size obtained by the device can be much smaller than the sample size obtained by current devices.

The inventors have devised a new protocol for preparing tissue samples for further analysis, wherein the tissue sample is much smaller than the tissue sample required for use in most known preparation and analysis methods. It has been found that, despite the small size of the tissue sample obtained/used, the protocol devised by the inventors allows for accurate and reproducible analysis and sampling of small tissue samples.

Therefore, according to another aspect of the invention, there is provided a method of analysing a tissue sample having a size of less than about 10 mg, optionally wherein the sample has been obtained according to the method as described herein or the use of the biopsy device as described herein. Preferably, the sample used in the method of analysing the tissue sample has previously been obtained by the biopsy device and/or the method described herein.

Advantageously, the tissue sample may have a size of less than about 9, 8, 7, 6, 5, 4, 3, 2, or 1 mg. Preferably, the tissue sample size is from about 0.01 mg to about 5 mg, such as from about 0.01 to about 1 mg, and about 0.01 to about 0.1 mg.

Conveniently, the analysis undertaken may be selected from the list consisting of histology, cytology, proteomics, transcriptomics and genetic analysis.

Preferably, after the sample is obtained, whether by use of the device according to the invention or by another device or method, the sample is immediately frozen, preferably by placing the tissue sample in a container and putting the container into contact with dry-ice so as to preserve the sample for further analysis. The term 'immediately' in this context means within 10 minutes of obtaining the tissue sample, such as within 9, 8, 7, 6, 5, 4, 3, 2, or 1 minute of obtaining the tissue sample. Most preferably, the tissue sample is placed in the container, which is then placed on dry-ice, in less than a minute of the sample being taken.

Advantageously, about 10 μL to about 200 μL of lysis buffer is added to the tissue sample, such as from about 10 μL to about 100 μL, preferably about 10 μL to about 50 μL. After which, the sample may be homogenized, preferably by vortexing on a benchtop vortexer for 1 to 60 seconds, such as 5 to 30 seconds and preferably from 10 to 20 seconds.

Conveniently, the sample is centrifuged, preferably on a benchtop micro-centrifuge, for 5 seconds to two minutes, such as from 5 seconds to 60 seconds, preferably from 5 seconds to 30 seconds.

Advantageously, the sample is homogenized and centrifuged as outlined above at least one further time, such as two, three, four or five further times.

Preferably, the samples are incubated for 10 to 60 minutes, such as 10 to 30 minutes, at a temperature of from 35° C. to 40° C., such as from 35° C. to 38° C.

Advantageously, the tissue sample is homogenised and centrifuged a further time according to the method outlined above, preferably the sample undergoes the homogenisation and centrifugation steps two further times.

Conveniently, about 25 μL to about 500 μL of buffer is added to the sample after homogenisation and centrifugation, such as from about 25 μL to about 250 μL, such as about 25 μL to about 100 μL.

Preferably, magnetic beads are then added to sample, wherein the magnetic beads are configured so as to bind RNA through solid phase reversible immobilisation on the surface of the magnetic beads. Under the following steps, the RNA is extracted from the tissue sample and binds to the surface of the magnetic beads so that the sample may be washed.

Advantageously, the sample undergoes another incubation step for about 5 to about 30 minutes, such as about 5 to about 25 minutes, preferably for about 5 to about 20 minutes at a temperature of from about 20° C. to about 40° C., such as about 20° C. to about 30° C., preferably about 20° C. to about 25° C.

Conveniently, the sample is placed on a magnet for about 5 to 30 minutes, such as about 5 to about 20 minutes. After which, the supernatant is preferably decanted.

Ideally, the sample is then washed, preferably several times (such as 2, 3, 4 or 5 times) with buffer. Preferably from about 20 μl to about 200 μl of buffer is added to the sample to wash it, such as from about 20 μl to about 100 μl of buffer, preferably from about 20 μl to about 80 μl of buffer. After which, the sample is placed on a magnet as outlined above and the supernatant is decanted.

Advantageously, the sample is then washed with an ethanol solution, preferably an ethanol solution comprising of from about 75 vol % to 95 vol % ethanol and about 25 vol % and 5% vol % water is used, such as from about 80 vol. % to about 90 vol. % ethanol and about 20 vol % and 10 vol % water. After which, the sample is preferably placed on a magnet as outlined above and the supernatant is decanted.

Preferably when washing with ethanol, the sample is washed with from about 50 μl to about 500 μl of the solution described in the preceding paragraph, such as from about 50 μl to about 200 μl, preferably from about 100 μl to about 200 μl.

Preferably, about 1 μL to about 100 μL of DNAse solution is added to the sample, such as about 1 μL to about 50 μL, preferably about 3 about 10 μl of DNAse solution.

After Adding DNAse, the sample is incubated for 5 to 30 minutes, such as 10 to 20 minutes, at a temperature of from 35° C. to 40° C., such as from 35° C. to 38° C.

Advantageously, from about 10 μl to about 200 μl of wash buffer is added to the sample, such as from about 10 μl to about 100 μl of wash buffer and, preferably, the sample is incubated for about 1 to about 20 minutes, such as about 1 to about 15 minutes, preferably for about 1 to about 10 minutes at a temperature of from about 20° C. to about 40° C., such as about 20° C. to about 30° C., preferably about 20° C. to about 25° C.

Conveniently, the sample is then placed on a magnet for about 1 minute to about 20 minutes, such as about 1 minute to about 10 minutes. After which, the supernatant is preferably removed.

Preferably, an ethanol solution is then added to the sample so as to wash the sample. Advantageously, the ethanol solution comprises from about 75 vol % to 95 vol % ethanol and about 25 vol % and 5% vol % water is used, such as from about 80 vol. % to about 90 vol. % ethanol and about 20 vol % and 10 vol % water. After which, the sample is preferably placed on a magnet as outlined above and the supernatant is decanted.

Preferably when washing with ethanol, the sample is washed with from about 50 μl to about 500 μl of the solution described in the preceding paragraph, such as from about 50 μl to about 200 μl, preferably from about 100 μl to about 200 μl.

Conveniently, after removing the supernatant, the magnetic beads are allowed to dry for a period of from about 1 minute to about 30 minutes, such as from about 1 minute to about 20 minutes, preferably from about 1 minute to about 10 minutes, at room temperature.

Advantageously, after drying the magnetic beads are resuspended in nuclease water so as to release the RNA that is bound to the surface of the magnetic beads. Preferably, the volume of nuclease water used is from about 1 μl to about 50 μl, such as about 1 μl to about 30 μl, for example from about 1 μl to about 20 μl, preferably from about 1 μl to about 10 μl.

Preferably, the resuspended beads are then incubated at room temperature for a period of from about 1 minute to about 10 minutes, such as about 1 minute to about 5 minutes and then returned to a magnetic stand.

Conveniently, the eluted RNA is then transferred to a fresh vessel for storage.

Specific embodiments of the invention will now be described with reference to the accompanying drawings.

Figure 2:
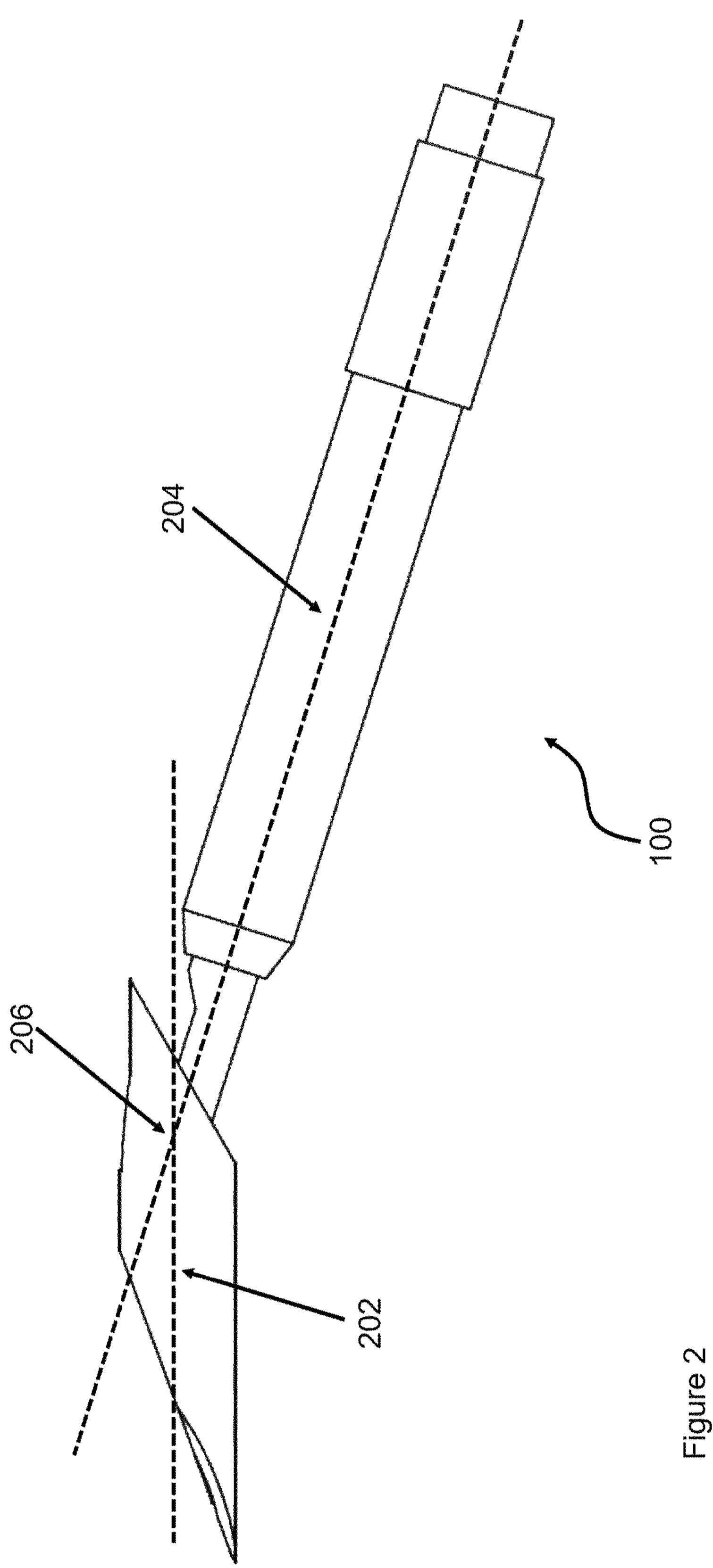
FIG. 2 is a side view of the biopsy device shown in Figure one with the first longitudinal axis of the rod member and the second longitudinal axis of the tip member being identified.
Figure 3:
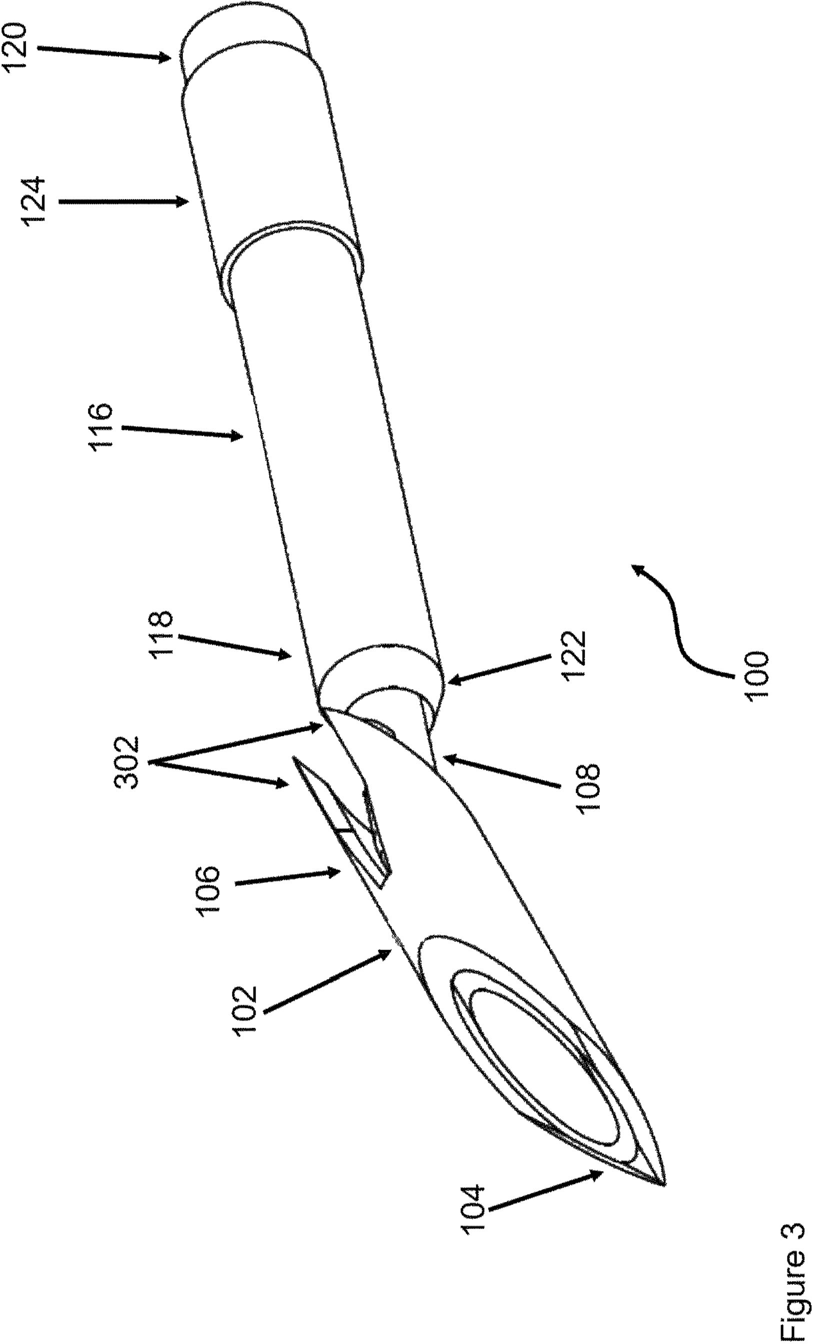
FIG. 3 shows the device of FIGS. 1 and 2 from a front perspective.

FIGS. 1 to 3 show an embodiment of the biopsy device (100) of the invention having an elongate flexible rod member (108) and a tip member (102). The flexible rod member comprises a distal end (110) and a proximal end (112) with the tip member (102) being located towards the distal end (110) of the rod member.

The tip member (102) also comprises a distal end (104) and a proximal end (106). In this embodiment, the distal end is in the form of a bevelled sharpened tip which is able to penetrate the tissue of a subject. From the angle provided in FIG. 1, the proximal cutting portion end of the tip member is also in a bevelled form, with the point of the proximal end being opposite to the point of the distal end of the tip so that on a side projection the tip member is in the shape of a parallelogram.

The distal end (104) and the proximal end (106) of the tip member (102) define a longitudinal axis (202) spanning the longitudinal length of the tip member (102), which is exemplified in FIG. 2. The distal end (110) and the proximal end (112) of the rod member (108) define a longitudinal axis (204) of the rod member when it is in a straight configuration.

The tip member is angularly offset with respect to the longitudinal axis of the rod member so that the longitudinal axes of the tip member and the rod member form a point where they intersect (206), which is denoted in FIG. 2.

FIG. 3 shows that the cutting portion of the proximal end of the tip member is in the form of two pointed blades (302) with a single edge, wherein the blades are spaced apart from each other to define a void. In this embodiment, the points of the blades extend parallel to one another in the proximal direction of the longitudinal axis of the tip member and the blade edges are facing one another.

The rod member (108) comprises a trough portion (114) which is positioned opposite to and facing the cutting portion (106) of the tip member so as to be located below the void between the two pointed blades (302).

The biopsy device of FIGS. 1 to 3 is configured so that the rod member (108) is slidably and rotatably disposed within the lumen of a sheath member (116), wherein the tip member (102) is not able to enter the sheath member (116) due to the angular offset between the longitudinal axes of the tip member and rod member and the tip member (102) abuts the opening of the sheath member (116) when the rod member (108) is retracted. The sheath member comprises a distal end (118) and a proximal end (120), with the distal end comprising a bevelled cutting edge (122) disposed symmetrically around the entire lumen at the edge of the distal end.

Towards the proximal end of the sheath member (120), there is located a collar (124) which acts as an intrusion depth limitation member so as to allow control over the maximum depth to which the sheath member may be advanced into the tissue of a subject.

In use, the device is directed towards the bodily site of a subject either independently or through the use of a guiding catheter, or a similar commonly used device. On reaching the bodily site of interest, the biopsy device is advanced towards the body tissue and the pointed tip member, which is always located outside of the sheath member, penetrates the tissue. At this point, the rod member is in a fully retracted position within the sheath member so that the cutting edge of the distal end of the sheath member abuts the proximal end of the tip member.

On penetrating the tissue, the device is further advanced into the tissue and is either halted at a desired position or advancement is halted when the collar on the sheath reaches the tissue and resists any further penetration of the sheath into the tissue.

In this embodiment, the tip member and rod member are rigidly fixed to one another so that the longitudinal axis of the tip member is permanently offset with respect to the longitudinal axis of the rod member. However, it is also envisaged that the device may be configured so that the longitudinal axes of the tip member and rod member extend along predominantly the same line when the device is penetrated into the tissue and that only once the tip has reached the desired depth is the tip member pivoted so as to angularly offset to the rod member.

Upon reaching the desired depth, the tip and rod member are further advanced into the tissue by slidably advancing the rod member out of the sheath member so that the trough of the rod member is uncovered.

To obtain the sample, the rod and tip member are rotated and then retracted back within the sheath member, where the bevelled cutting edge located at the distal end of the sheath member acts as a second cutting edge to slice the tissue from the opposite direction to the cutting portion of the tip member.

The retraction is continued until the rod member is once again fully housed within the sheath member and the distal end of the sheath member abuts the proximal end of the tip member. This action results in a sample of tissue being contained within the trough of the rod member which is partly housed in the sheath, or, if the tissue sample size is larger than the trough, the tissue sample may be trapped within the trough region by the cutting portion.

As a slight variation of the method, rather than the rotation and retraction of the tip member occurring sequentially, these steps may occur simultaneously.

The device and method of using the device result in a uniform sample of predicted size being housed within the trough of the rod member with minimal damage to the tissue being made. However, when larger samples of tissue are required, then it is envisaged that the rod member is not retracted within the sheath after rotation and that after rotation, the device is retracted entirely from the body of the subject bringing with it a larger sample size of the tissue.

EXAMPLES

The present invention will be further described by reference to the following examples which are not intended to limit the scope of the invention.

Manufacturing Method of Device

Provided below is an exemplary method for manufacturing the device according to the invention. The device of the invention prepared by this exemplary method is made up of three parts; a) the tip member which is an approximately 2 mm long grinded and laser cut section of nitinol tube, b) the rod member which is manufactured from a nitinol wire, to which the tip member is attached, and c) the sheath member nitinol housing part with a grinded, distal end.

Nitinol is a well-recognized term in the art and is a nickel-titanium alloy distinguished from other materials by its shape memory and super elastic characteristics.

The material used to construct the biopsy device of the invention may be nitinol tubes with an outer and inner diameter of 380 and 280 μm respectively, and nitinol wires with a diameter of 228 μm.

Figure 4:
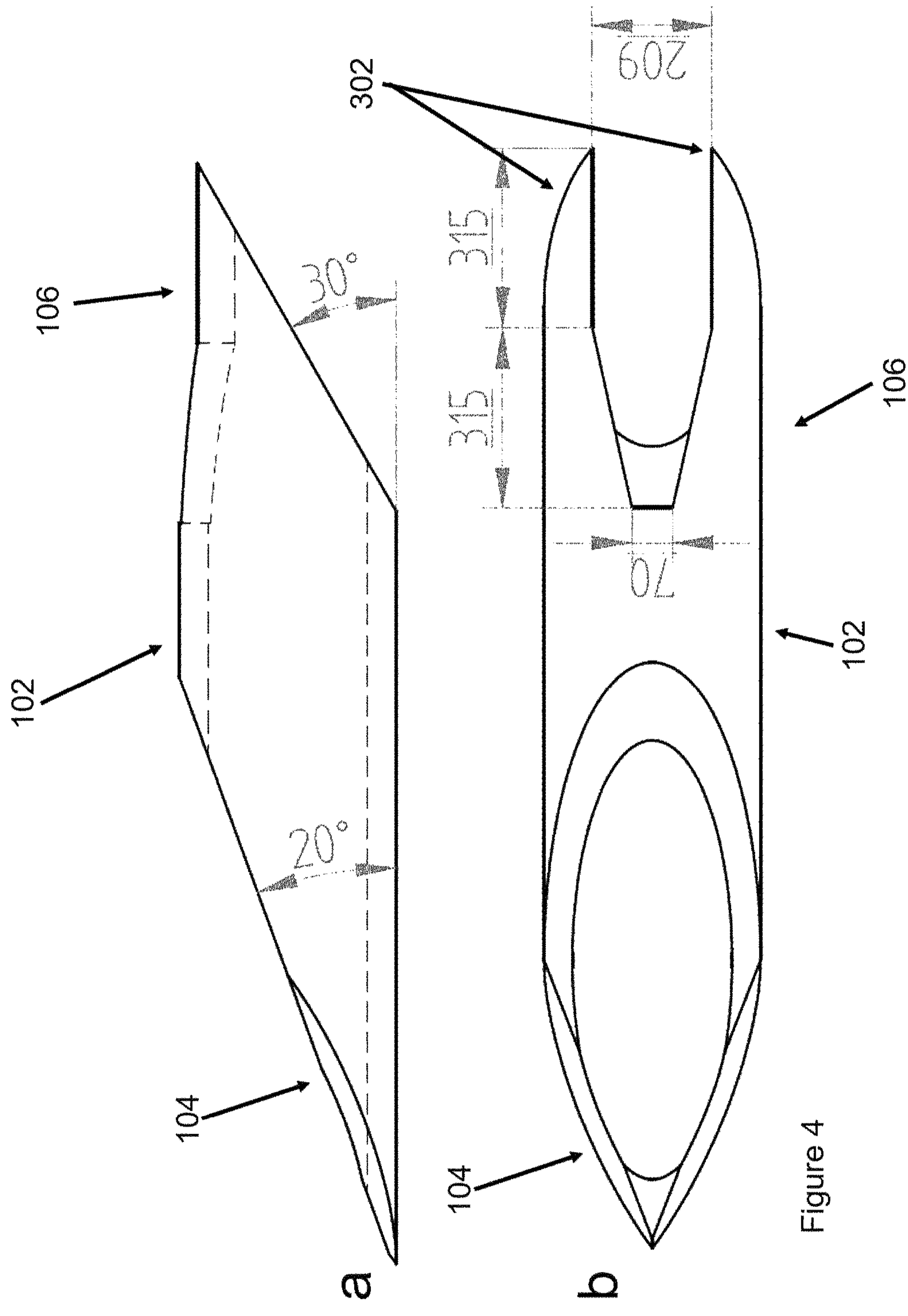
FIG. 4 shows multiple views of an embodiment of the tip member according to the invention.

In this exemplary method, the first step in creating the tip member (102) involves grinding the tubes with a 15° angle across the tubes cross section. The tube is rotated 45 degrees and a 20° grinding on each side is performed. The two grindings meet in a sharp point in the middle axis of the tube. The tube is subsequently laser cut at 2 mm from the tip of the grinding as illustrated in FIG. 4. After the proximal machining of the device is done it is rotated 90 degrees and cut off, producing two sharp edges at the proximal end (302).

After machining the tip member, it is then attached to a wire that has been manually bent with an angle between 16-19°. It is assembled on top of the wire and subsequently fixed in place with cyanoacrylate glue. Any cyanoacrylate residue is machined away with the laser. The tip of the device is sharpened with the laser, matching the grinding that was initially done. After assembly, the angle of the distal end of the tip member is around 20 degrees after assembly, as illustrated in FIG. 4. The wire is machined distally near the proximal end of the tip member to create a cavity (trough, (114)), as illustrated in FIGS. 1 and 3. The cavity is machined from the side and is cut in the shape of a parallelogram with dimensions as illustrated in FIG. 4.

The wire is placed inside the tube and the movement is controlled with a proximal torque device which allows rotation of the distal part and limits the translational movement.

The sheath member may be manufactured by grinding a 20° taper around the entire circumference of the distal end of a nitinol tube and subsequently gluing a gold collar 1-20 mm (depending on desired depth of sampling) from the distal end with cyanoacrylate glue. Any eventual grinding and cyanoacrylate residues were removed with the laser. The distal part of the device, attached to the wire, was placed inside the proximal end of the sheath member by reverse mounting and the movement of the distal part was controlled with a torque device attached to the wire which allowed rotation of the distal part and limited the translational movement. The whole device was designed to be housed in a clinically available 2.7F high-flow micro-catheter to provide support and to shield the sharpened tip during navigation through the body.

Sampling Procedure

All devices tested in the sampling procedure consisted of a conically sharpened housing part (sheath member) and a wire (rod member) attached to a cutting tip (tip member) at the distal end that was advanced into the endomyocardium of swine and then rotated and the retracted to "pinch off" a small tissue sample wedging it in a collecting pocket, as the device system was retracted through the guide catheter.

The weight of five samples obtained by the device were measured and the average mass of the sample obtained was 0.052 mg, with the individual weights being 0.04, 0.04, 0.09, 0.06 and 0.03 mg.

A depth-limiting collar provides visibility on fluoroscopy and minimizes risk of accidental perforation of the ventricle wall. As the device was removed from the body, microsurgical forceps were used to extract the tissue sample under microscopy monitoring and immediately stored on a microscope slide for histology or in a 0.2 ml PCR tube if molecular analysis was desired. While extracting the tissue piece from the micro-bioptome, it was examined using a surgical or dissection microscope and given a size score (1-4, evaluated by a single operator) based on size, appearance and texture. The scoring system is described in table 1 below.

TABLE 1

| Yield score | Description | % with optimal device design |
|---|---|---|
| 1 | Minimal tissue, often fragmented. | 14 |
| 2 | Small but intact tissue piece, barely visible without surgical microscope. | 29 |
| 3 | Medium sized piece protruding from sample pocket of device. Clearly visible without microscopy. | 43 |
| 4 | Large piece that could be handled without surgical microscope. | 14 |

Evaluation Ex Vivo and in Simulator

Ex vivo histological evaluation was performed using the device on post-mortem myocardium, to evaluate yield.

Devices were also tested in a custom-made simulator, constructed from plastic tubing and an acrylic glass chamber, where navigation and sampling using the prototypes could be evaluated in a realistic anatomical situation.

In Vivo Evaluation

Iterative in vivo evaluation of the devices was performed in a swine model in a fully-equipped, clinical grade 3D-angiocatheterization laboratory in 23 adult swine weighing an average of 37 kg, with the range of weights being 29-48.5 kg. Briefly, animals were pre-medicated with sedatives and taken to a clinical angiography suite, intubated and mechanically ventilated while receiving standard surgical anesthetic care.

Throughout intervention, the animals were monitored for complications using ECG, invasive blood pressure measurement, oxygen saturation, temperature, and urine production. Animals were treated with 75 mg amiodarone i.v., and an additional dose of 75 mg if the duration of the intervention surpassed 3 hours. Initial devices were tested using transjugular access to the right ventricle using an 8.6F deflectable sheath (Agilis NXT, Saint Jude Medical, Saint Paul, MI, USA). As the devices were miniaturized, they were tested in both ventricles including the left ventricle (LV). All left ventricular biopsies were obtained using transfemoral approach.

A 5F or 7F short sheath was used to gain access to the femoral artery, and a standard 5F or 4F straight diagnostic catheter (Torcon NB advantage, Cook Medical, USA) was used to access the LV and from there the 2.7 French micro-catheter housing the bioptome, was advanced. Biopsy controls were obtained using a standard endomyocardial forceps bioptome (3F or 5.2F Flexible Myocardial Biopsy Forceps, Cook Medical, USA or 6F Jawz Endomyocardial Biopsy Forceps, Argon Medical Devices, Frisco, TX, USA). Whole blood, and skeletal muscle from the limb, was also obtained as control tissue for sequencing. From some pigs, the endocardial layer of the left ventricle was scraped off as additional control samples. After sampling, animals were sacrificed using overdose of sodium pentobarbital.

Follow-Up Evaluation In Vivo

In 6 swine, weighing between 27-31.9 kg, with an average weight of 28.75 kg, the inventive device was evaluated alone (n=3) or in conjunction with a conventional endomyocardial biopsy (n=3) for safety during a 7-day follow-up period. The animals were recruited sequentially, but the group was pre-specified before start of anesthesia and intervention. Animals were housed in a dedicated large-animal housing facility with dedicated staff trained in large animal husbandry and clinical monitoring, supervised by veterinarian. The initial procedure was performed as in the non-follow up group, with the exception of using inhalation anesthetic (isoflurane) rather than sodium pentobarbital. After intervention, the animals were awoken from anesthesia and housed for 7 days, receiving standard post-operative care, and monitored for complications. At day 7, a follow-up intervention was performed with additional micro-biopsies and conventional biopsies, after which the animals were sacrificed and the heart examined. A subset of samples were sequenced using RNA-seq and longitudinal variation in mRNA expression was evaluated.

Histology

Micro-biopsy samples obtained in the in vivo evaluation study were too small to reliably section onto slides. Instead, tissue pieces were placed directly on to microscope slides and compressed in a manner similar to the preparation of cytological specimens. Slides were stained using May-Grünwald-giemsa or immunohistochemistry using the indirect fluorescence method to stain for troponin I (Rabbit-anti-pig primary antibody, Abcam, Cambridge, UK).

RNA Isolation and Sequencing

RNA from animals in the in vivo evaluation group was isolated processed and sent for RNA-sequencing. In a pilot round of sequencing, 24 samples were sequenced, including controls consisting of whole blood and myocardium from conventional biopsy. The results were subsequently confirmed with a second round of sequencing of 57 samples from 5 individual pigs, adding skeletal muscle and endocardial tissue as additional controls. For sample handling and RNA isolation, in general the following protocol was used.

In general the sampling protocol used was as follows. Immediately upon biopsy device retraction, the tissue sample was transferred from the biopsy device to a 0.2 ml PCR tube with micro-forceps. The sample was immediately put on dry ice and frozen until further processing.

31 μL of proprietary lysis buffer was added to the sample and the tissue sample was then disrupted and homogenized by vortexing on benchtop vortexer for 15 seconds. After which, the sample was centrifuged on benchtop microcentrifuge for 15 seconds. This procedure was repeated twice. The sample was then incubated for 25 minutes at 37° C., after which the sample was vortexed and centrifuged as detailed above a further two times.

52.3 μL of proprietary bind buffer (kit), including magnetic beads, was added to sample and the sample was incubated for 10 minutes at room temperature.

After incubation, the sample was placed on a magnet for 6 to 20 minutes until the solution turned clear and the supernatant was subsequently decanted.

The sample was then washed several times by adding 77 μl of proprietary wash buffer (kit), pipetting the solution, placing on a magnet for 5 minutes and decanting the supernatant.

100 μl to 200 μl of 85 vol % ethanol was then added and the sample was mixed, placed on a magnet and the supernatant was subsequently removed.

Optionally, (depending on the downstream library preparation protocol) 7.7 μl of DNAse solution was added and the sample was incubated at 37° C. for 15 minutes.

42.3 μl of wash buffer was added and the sample was incubated at room temperature for 4 minutes, placed on a magnet for 7 minutes, after which, the supernatant was removed.

100-200 μl 85 vol % ethanol was added to the sample and the sample was placed on a magnet for 5 minutes. The supernatant was then removed and the washing step was repeated two or three times. The magnetic beads were then allowed to dry for 5 minutes at room temperature.

The magnetic beads were then resuspended in 3-10 μl nuclease water and incubated at room temperature for 2 minutes and then returned to the magnetic stand. The eluted RNA was then transferred to a fresh plate or tube for storage.

The totalRNA was then processed with either of a couple of combinations of kits and protocols, modified or as is, and sequenced on a sequencing platform, e. g. Illumina as used in our studies for proof-of-concept.

Libraries were also prepared using combinations of kits and protocols, either modified or used as standard.

Data Analysis and Statistical Methods

Statistical analysis was performed using the R statistical computing language, version 3.4.1 (Vienna, Austria, https://www.R-project.org/). Descriptive statistics are presented as median (range) unless otherwise specified. RNA-seq data benchmarked and processed using STAR, Cutadapt, FastQC for quality control and finally R for higher-level statistics.

Figure 5:
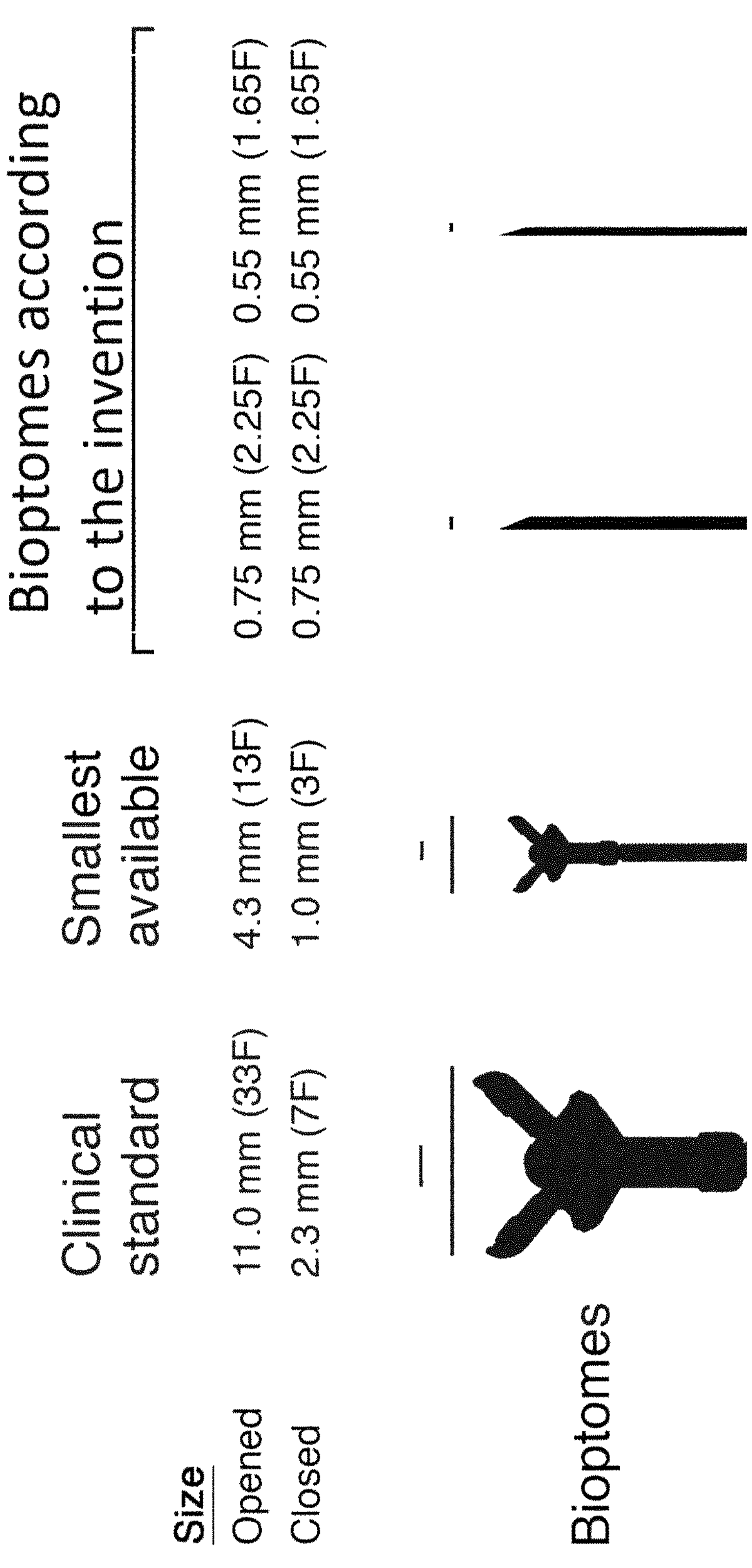
FIG. 5 shows a size comparison between currently used bioptomes and the scale to which the present inventive device may be manufacture to whilst still being usable for obtaining a biopsy sample.

Results of Micro-Bioptome Design 65 prototype designs were evaluated, all based on a core principle of a sharpened housing part containing a wire with a cutting tip that penetrates the myocardium and "pinches off" a small piece of tissue. The final device design had an OD of approximately 0.4 mm (0.68 mm at the radioopaque marker), and was housed in a 2.7F high-flow micro-catheter designed for embolization (Renegade Hi-Flo, Boston Scientific, Marlborough, MA, USA or Carnelian, Tokai Medical Products, Aichi, Japan). An angled tip "guide" catheter was used, allowing the micro-bioptome system to be steered and navigated inside the heart. In the current protocol, a 4F or 5F standard diagnostic catheter was used as "guide" catheter for the micro-catheter containing the device. Iterative improvements to the design increased the biopsy success rate, yield (measured using the qualitative scoring system), and ease-of-use of the device. The final design, used for the in vivo follow-up study, is illustrated in FIGS. 1 to 3. FIG. 5 shows a comparison of the size that the bioptomes according to the invention can be manufactured to whilst still being suitable for obtaining good tissue samples with respect to currently used clinical devices.

Results of In Vivo Study

Micro-biopsies and conventional biopsies were successful in all animals (n=6, n=3 for combined prototype- and conventional biopsy). Using the inventive device, a success rate of 94% was achieved. For unknown reasons, all animals in this study had tachycardia before start of intervention, and had an increased tendency for transient ventricular arrhythmia, compared to the non-follow up group.

All animals tolerated the micro-biopsy procedure well however, and no specific treatment was needed at this stage. In animals where conventional biopsies were performed, it was difficult to navigate the biopsy forceps across the aortic arch and into the LV. One animal had sustained ventricular tachycardia for approximately 60 minutes, starting after the final conventional biopsy. 300 mg amiodarone i.v. was given, after which the animal stabilized and could be awoken without complications. Another animal in which both types of biopsy were performed was stable during the intervention, but developed respiratory insufficiency and subsequent cardiac arrest shortly after waking from anesthesia. Gross pathologic evaluation showed a small heart with abnormally small LV, consistent with cardiomyopathy. This animal was therefore excluded from subsequent analyses. All animals had small amounts (<10 ml) of blood-tinged pericardial effusion, and visible marks at the sites of biopsy. There were no macroscopic signs of infarction or ventricular rupture on gross examination of the heart in any animal.

In summary, all three animals that underwent repeated heart biopsies with our novel device, were successfully woken up and brought back to the angiography suite after seven days for additional sampling. Of the three animals that underwent heart biopsies with both our novel device and a conventional device, two were successfully woken up and brought back for follow-up sampling.

Results of Tissue Identification by Histology and Immunohistochemistry

Figure 6:
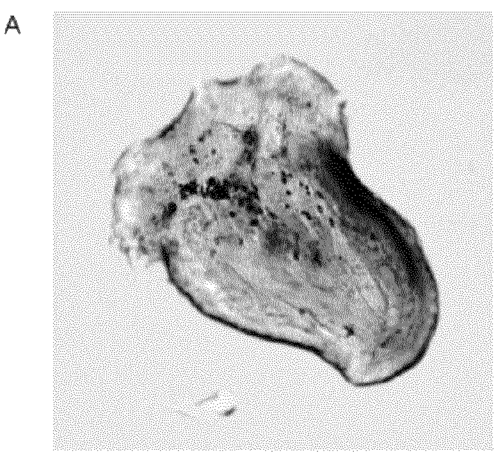
FIG. 6A shows a tissue sample that has been obtained by the device of the invention and stained with a May-Grünwald-giemsa stain.
FIG. 6B shows a stained tissue sample obtained by the device of the invention to confirm the presence of troponin I in the tissue.
FIG. 6C shows a tissue sample with striation being highlighted.
Figure 6:
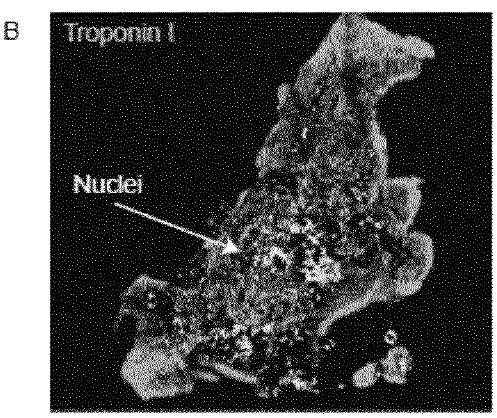
Figure 6:
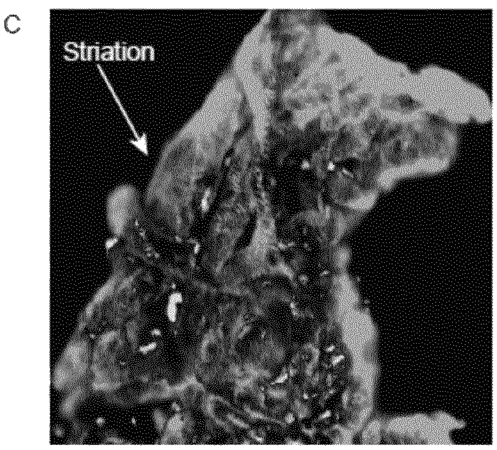

To verify that samples contained only myocardial tissue, histology and immunohistochemistry was performed on a subset of samples. May-Grünwald-giemsa stain showed solid tissue pieces with considerable crush artifacts (FIG. 6A). Thick layering of unsectioned tissue in most samples precluded evaluation of pathology. In many cases, the sample could not readily be identified as myocardial tissue. Therefore, immunohistochemistry was used to confirm the presence of troponin I in the tissue pieces (FIGS. 6B and 6C).

Results of RNA Sequencing

Figure 7A:
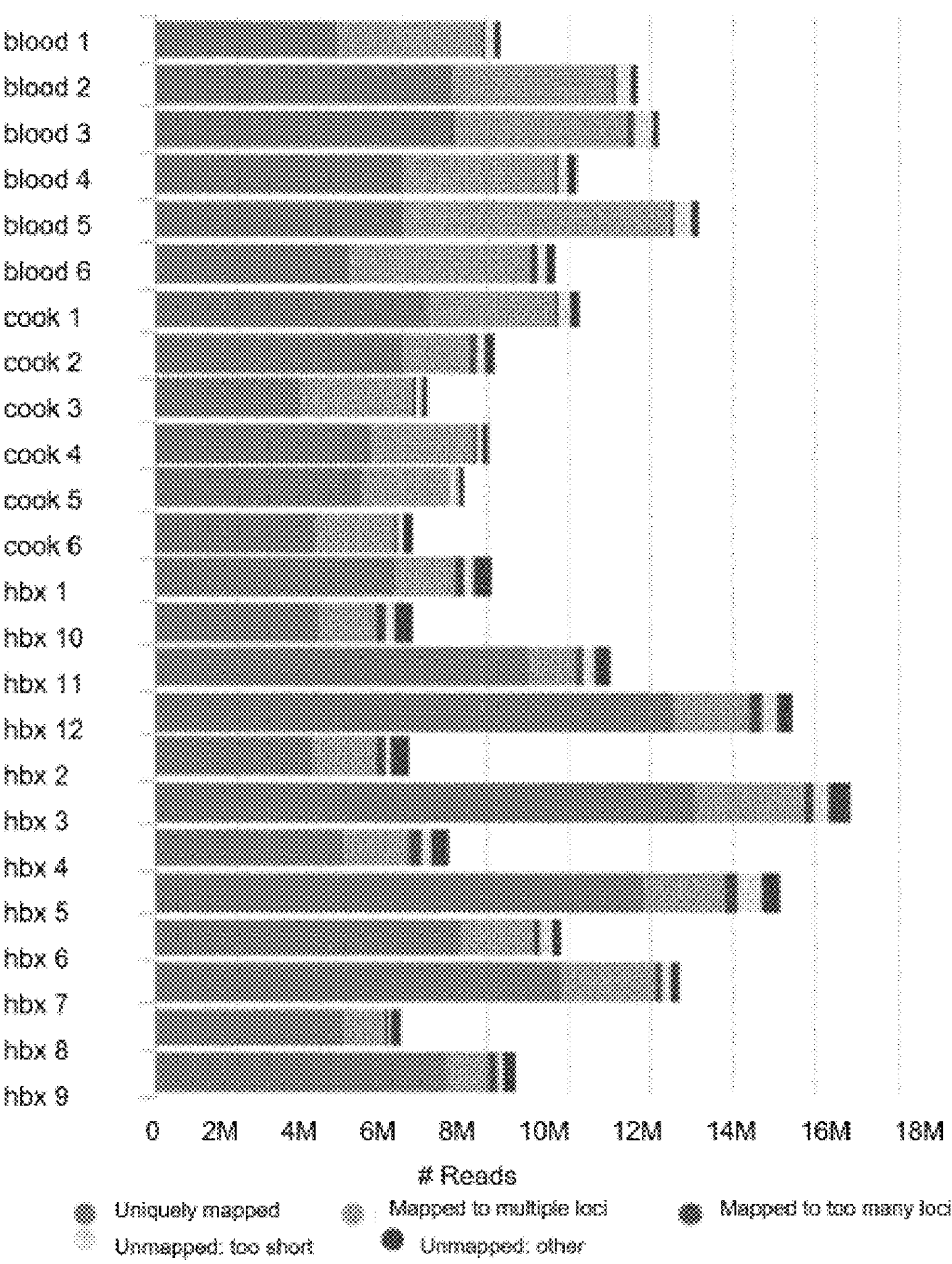
FIGS. 7A and 7B show the alignment scores of 24 sample microbiopsies obtained by the device of the invention.
Figure 7B:
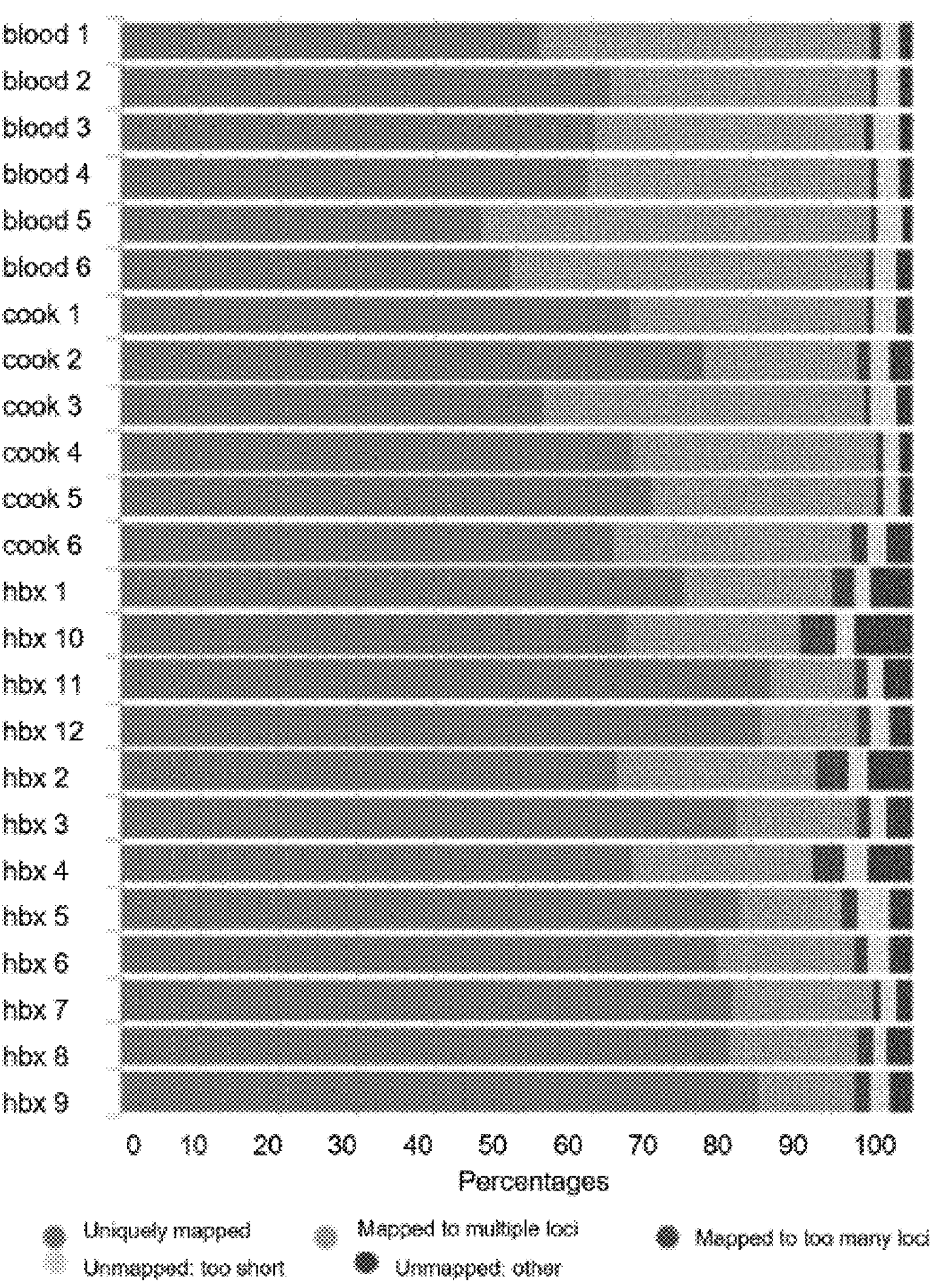
Figure 8A:
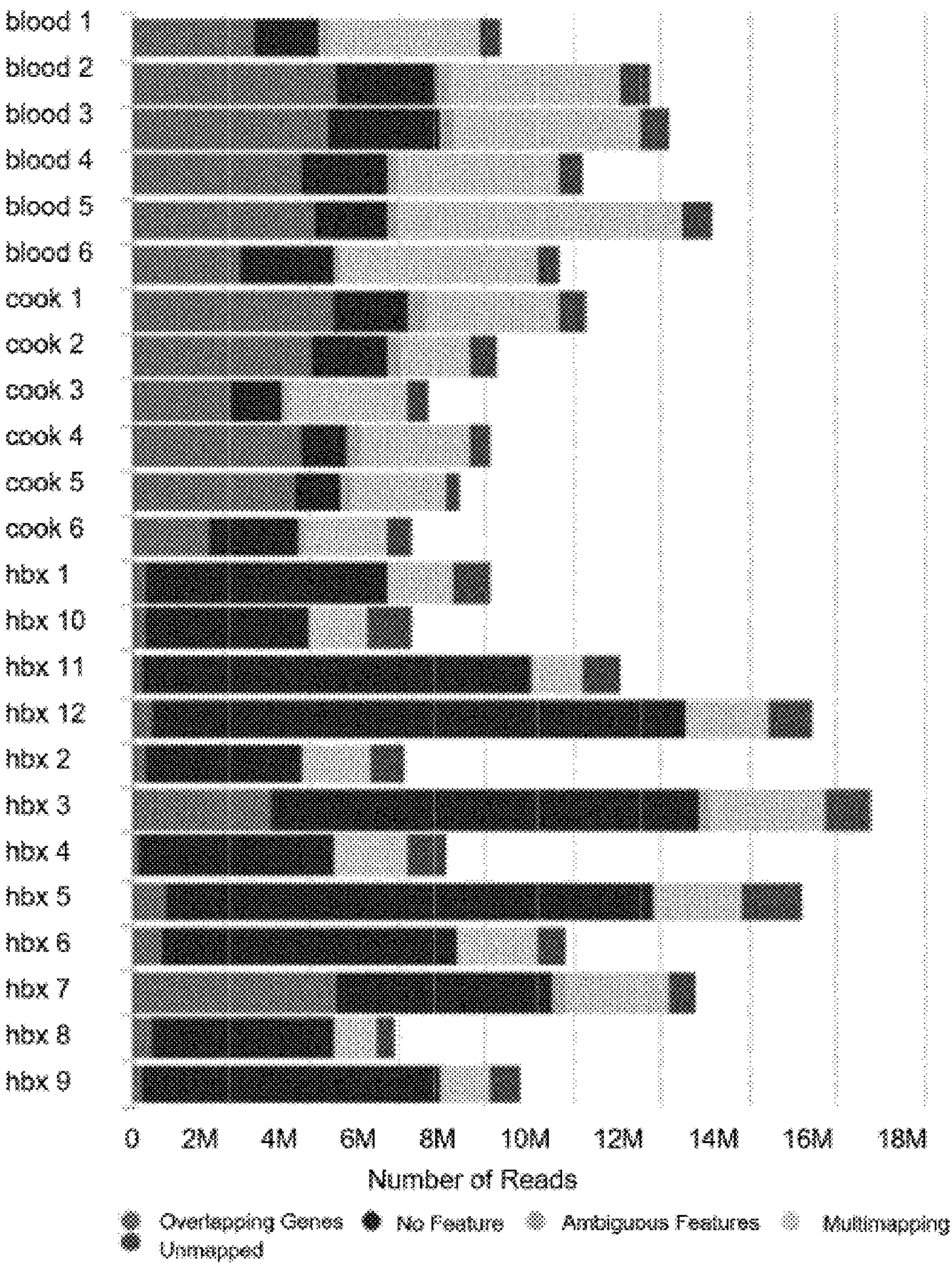
FIGS. 8A and 8B show the gene mapping of the 24 samples of FIGS. 7A and 7B.
Figure 8B:
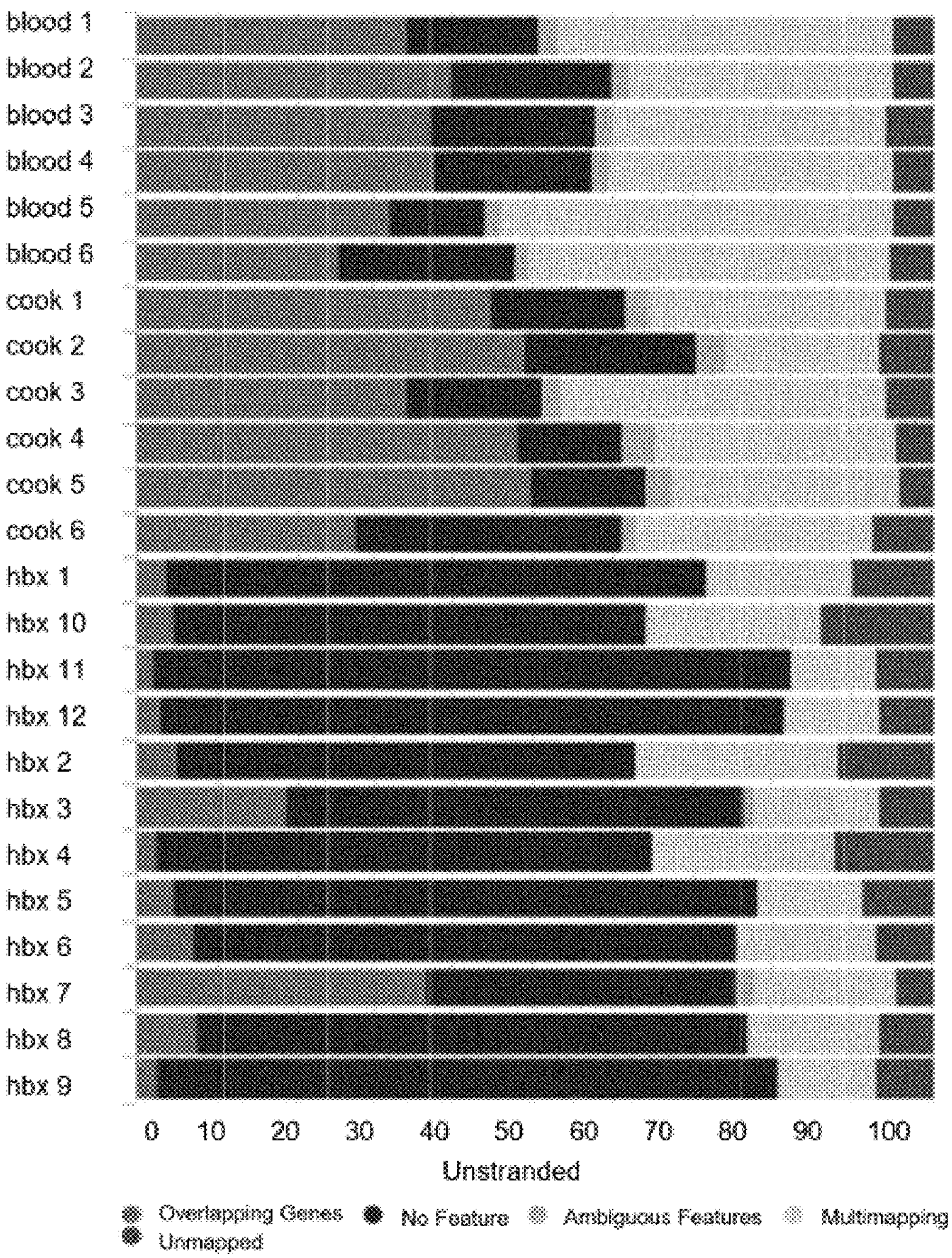

RNA sequencing was successful for all 24 samples submitted to the sequencing facility in the first round of sequencing. The alignment scores were relatively consistent across micro-biopsies and controls (see FIGS. 7A and 7B). Gene mapping varied between myocardial samples and blood controls, with most myocardial samples having a lower proportion of reads mapped to genes, and a large proportion of reads mapping to unknown features (FIGS. 8A and 8B). The rates of multimapped and unmapped reads between myocardial samples obtained with prototype or conventional were comparable.

In the following round of sequencing, all 57 samples were successful in terms of number of reads and overall read quality. However, one heart biopsy sample was excluded due to low mapping rate towards the pig genome. Additional five samples, out of which three samples were taken with the novel instrument, were excluded due to low library complexity. In total 51/57 samples were used for gene expression analysis. Table 2 shows baseline quality control data.

TABLE 2

| Sample Name | % Aligned | Reads aligned (M) | % Trimmed | % Duplicate reads | % GC-content | Sequences (M) |
|---|---|---|---|---|---|---|
| blood1 | 53.2% | 4.4 | 1.3% | 62.3% | 49% | 8.3 |
| blood2 | 62.3% | 7.3 | 1.5% | 58.8% | 48% | 11.6 |
| blood3 | 60.2% | 7.3 | 1.5% | 61.4% | 46% | 12.2 |
| blood4 | 59.6% | 6.1 | 1.4% | 60.5% | 47% | 10.2 |
| blood5 | 46.2% | 6.1 | 1.6% | 75.6% | 50% | 13.1 |
| blood6 | 49.6% | 4.8 | 1.3% | 61.3% | 48% | 9.6 |
| cook1 | 64.8% | 6.6 | 1.3% | 70.0% | 45% | 10.2 |
| cook2 | 74.3% | 6.1 | 1.2% | 61.6% | 44% | 8.2 |
| cook3 | 53.9% | 3.6 | 1.4% | 67.7% | 45% | 6.6 |
| cook4 | 65.4% | 5.3 | 1.4% | 67.3% | 45% | 8.0 |
| cook5 | 67.6% | 5.0 | 1.3% | 63.1% | 45% | 7.4 |
| cook6 | 62.9% | 3.9 | 1.3% | 49.1% | 43% | 6.2 |
| hbx1 | 71.9% | 5.8 | 1.2% | 18.1% | 39% | 8.1 |
| hbx10 | 64.5% | 4.0 | 1.2% | 18.1% | 40% | 6.2 |
| hbx11 | 82.7% | 9.1 | 1.1% | 11.6% | 39% | 11.0 |
| hbx12 | 81.7% | 12.6 | 1.2% | 14.6% | 41% | 15.4 |
| hbx2 | 63.1% | 3.9 | 1.3% | 21.0% | 42% | 6.1 |
| hbx3 | 78.2% | 13.1 | 1.2% | 28.1% | 42% | 16.8 |
| hbx4 | 65.2% | 4.6 | 1.3% | 17.9% | 40% | 7.1 |
| hbx5 | 78.6% | 11.9 | 1.3% | 15.4% | 45% | 15.1 |
| hbx6 | 75.8% | 7.5 | 1.4% | 17.7% | 44% | 9.8 |
| hbx7 | 78.1% | 9.9 | 1.2% | 43.6% | 43% | 12.7 |
| hbx8 | 77.5% | 4.6 | 1.1% | 16.9% | 41% | 5.9 |
| hbx9 | 81.2% | 7.1 | 1.1% | 11.2% | 40% | 8.7 |

Results of Transcriptomic Analysis

Figure 9:
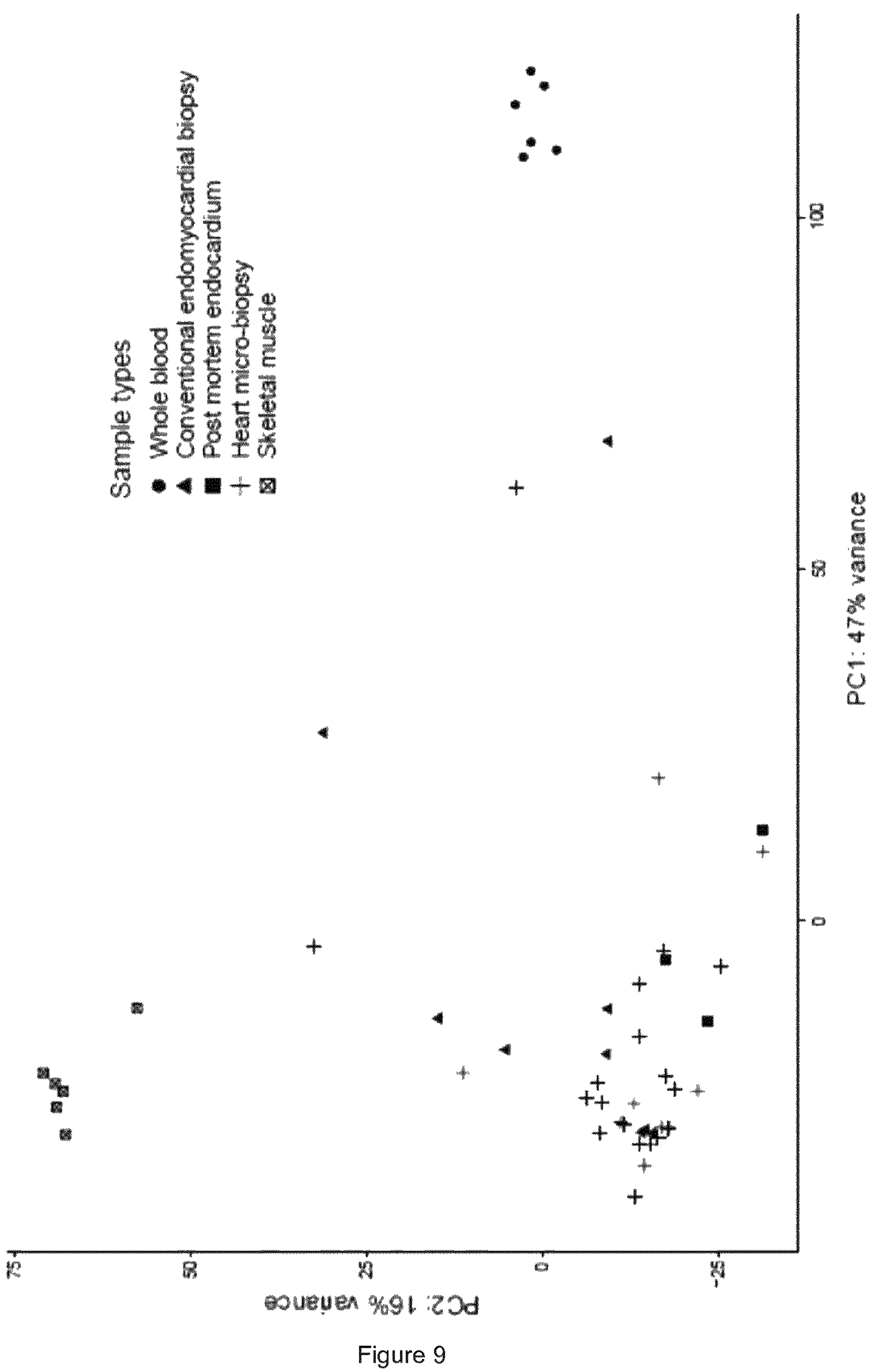
FIG. 9 shows the results of PCA analysis of tissue samples obtained by the device of the invention.

To further confirm the tissue type of micro-biopsy samples, principal component analysis (PCA) was performed, and the clustering pattern with controls was assessed (FIG. 9). Micro-biopsies of myocardium clustered closer to conventional biopsies of myocardium than whole blood. Skeletal muscle formed a distinct cluster, separate from blood and heart samples. Endocardial tissue was clustering together with the heart biopsy samples. There was a larger spread among micro-biopsies than conventional biopsies of myocardium. Individual sample-to-sample comparisons showed high abundance of expected transcripts, e.g. MYH7 in heart samples, MYH8 in skeletal muscle samples and haemoglobin related transcripts in blood. Gene ontology of the top differentially expressed genes in heart muscle (compared to blood) showed an enrichment of genes related to cardiomyocyte function and development in micro-biopsy samples.

The invention claimed is:

1. A biopsy device comprising:

an elongate flexible rod member having a proximal end and a distal end that define a first longitudinal axis; and a tip member having a proximal end and a distal end that define a second longitudinal axis, the tip member being located at or towards the distal end of the elongate flexible rod member, wherein the tip member and the elongate flexible rod member are rigidly fixed to one another at a coupling, wherein the coupling is configured to secure the tip member relative to the elongate flexible rod so that:

the second longitudinal axis of the tip member remains permanently angularly offset relative to the first longitudinal axis of the elongate flexible rod member at a fixed predetermined angle from insertion of the tip member into a body of a patient through removal of the tip member from the body of the patient; and the distal end of the tip member remains a fixed distance from an intersection between the first and second longitudinal axes from the insertion of the tip member into the body of the patient through the removal of the tip member from the body of the patient, wherein the distal end of the tip member is configured to penetrate tissue of a subject and the proximal end of the tip member comprises a cutting portion for cutting tissue of the subject.

2. The biopsy device according to claim 1, wherein the fixed predetermined angle is from about 1° to about 80°.

3. The biopsy device according to claim 1, wherein the cutting portion of the tip member comprises a pointed blade, wherein the point of the blade extends substantially in the proximal direction of the second longitudinal axis of the tip member.

4. The biopsy device according to claim 1, wherein the cutting portion of the tip member comprises two pointed blades, wherein the points of the blades extend in the proximal direction of the second longitudinal axis of the tip member.

5. The biopsy device according to claim 4, wherein the blades extend parallel to one another in the proximal direction of the second longitudinal axis of the tip member.

6. The biopsy device according to claim 5, wherein the blades are single blades that are facing each other, wherein the blades are spaced apart from each other so as to define a void in the cutting portion between the blades.

7. The biopsy device according to claim 1, wherein the elongate flexible rod member comprises a trough located at its distal end.

8. The biopsy device according to claim 7 wherein the trough of the elongate flexible rod member is positioned opposite to and facing the cutting portion and/or a void in the cutting portion of the tip member.

9. The biopsy device according to claim 1, wherein the elongate flexible rod member is slidably and rotatably disposed within the lumen of a sheath member, wherein the sheath member comprises a proximal end and a distal end, with the elongate flexible rod member extending from the distal end of the sheath member.

10. The biopsy device according to claim 9, wherein the sheath member comprises an anvil such that it can form a blade and anvil relationship with the cutting portion of the tip member in use.

11. The biopsy device according to claim 10, wherein the anvil extends around at least part of the entire edge of the lumen at the distal end of the sheath member.

12. The biopsy device according to claim 9, wherein the sheath member comprises a collar which acts as intrusion depth limitation member located proximally of the distal end.

13. The biopsy device according to claim 1, wherein the distal end of the tip member is in the form of a bevelled tip at an acute angle with respect to the second longitudinal axis of the tip member for penetrating the tissue of a subject.

14. The biopsy device according to claim 12, wherein the collar is comprised of a metal.

15. The biopsy device according to claim 1, wherein at least one of the tip member, the elongate flexible rod member and/or the sheath member are composed of a shape memory alloy.

16. A kit-of-parts comprising the biopsy device according to claim 1 in the form of a sterile, pre-packaged kit-of-parts for single use.

17. The kit-of-parts according to claim 16, where the kit further comprises a micro-catheter and/or a guide catheter, wherein the micro-catheter and/or guide catheter is in the same pack as the biopsy device or in a separate pack.

18. A method for obtaining a biopsy from a subject, wherein the method comprises:

delivering the device according to claim 1 to a body location within the body of the patient;

advancing the distal end of the tip member of the device into a tissue so that an entirety of the tip member advances into the tissue; and withdrawing the tip member from the tissue.

19. The method according to claim 18, wherein after penetrating the tissue and prior to retraction, the tip member is rotated in the tissue.

20. The method according to claim 18, wherein the elongate flexible rod member is slidably and rotatably disposed within the lumen of a sheath member, wherein the sheath member comprises a proximal end and a distal end, with the elongate flexible rod member extending from the distal end of the sheath member, and wherein on advancing the tip member into the tissue, the elongate flexible rod member is retracted within the sheath member so that the proximal end of the tip member abuts the distal end of the sheath member.

21. The method according to claim 20, wherein after advancing the tip member into the tissue, the elongate flexible rod member is extended out of the sheath portion and penetrated further into the tissue.

22. The method according to claim 21, wherein upon withdrawing the tip member from the tissue, the elongate flexible rod member is first retracted into the sheath portion, optionally wherein the biopsy device comprises an anvil which, on retraction of the elongate flexible rod member, provides a blade and anvil relationship with the cutting portion of the tip member in use.

23. The biopsy device of claim 1, wherein the cutting portion of the tip member is configured to cut tissue when moving in a proximal direction along the first longitudinal axis, and wherein the proximal end of the tip member is located proximally to the coupling between the tip member and the elongated flexible rod member.

* * * * *